(12) United States Patent
Yamauchi et al.

(10) Patent No.: US 7,526,388 B2
(45) Date of Patent: Apr. 28, 2009

(54) METHOD OF SELECTING AND ANALYZING SCRAP SILICON

(75) Inventors: Norichika Yamauchi, Ichihara (JP); Takehiko Shimada, Yokohama (JP)

(73) Assignee: IIS Materials Corporation, Ltd., Tokyo (JP)

( * ) Notice: Subject to any disclaimer, the term of this patent is extended or adjusted under 35 U.S.C. 154(b) by 203 days.

(21) Appl. No.: 11/434,515

(22) Filed: May 16, 2006

(65) Prior Publication Data

US 2007/0026539 A1 Feb. 1, 2007

(30) Foreign Application Priority Data

May 18, 2005 (JP) ............................. 2005-174244

(51) Int. Cl.
*G01R 15/00* (2006.01)
(52) U.S. Cl. ..................... 702/40; 250/370.09
(58) Field of Classification Search ............... 702/23, 702/35–40, 57–59; 438/14–18; 250/370.01, 250/370.09
See application file for complete search history.

(56) References Cited

U.S. PATENT DOCUMENTS

| | | | | |
|---|---|---|---|---|
| 4,065,742 A | * | 12/1977 | Kendall et al. | ................. 338/9 |
| 4,329,699 A | * | 5/1982 | Ishihara et al. | ................ 257/55 |
| 4,359,372 A | * | 11/1982 | Nagai et al. | ............ 204/192.21 |
| 5,200,619 A | * | 4/1993 | Asoka kumar et al. | ...... 250/307 |
| 5,346,557 A | * | 9/1994 | Ito et al. | ....................... 134/10 |
| 5,612,571 A | * | 3/1997 | Satou et al. | ................. 257/757 |
| 6,177,166 B1 | * | 1/2001 | Ohno et al. | ................ 428/64.1 |
| 6,638,778 B1 | * | 10/2003 | Peterson et al. | ............... 438/14 |
| 7,077,901 B2 | * | 7/2006 | Nakagawa et al. | ............ 117/54 |
| 7,258,741 B2 | * | 8/2007 | Linares et al. | ................ 117/86 |
| 2004/0022355 A1 | * | 2/2004 | Kaiser et al. | .................. 378/49 |
| 2005/0028840 A1 | * | 2/2005 | Lee et al. | ...................... 134/18 |

* cited by examiner

*Primary Examiner*—Eliseo Ramos Feliciano
*Assistant Examiner*—Mary C Baran
(74) *Attorney, Agent, or Firm*—Michael Tobias

(57) ABSTRACT

Non-destructive testing is performed on individual pieces of scrap silicon using an energy dispersive x-ray fluorescent analyzer to determine from the obtained spectral data whether a prescribed impurity element is contained therein. The electrical resistivity of each piece of scrap silicon can be measured, and the concentration of the impurity element contained in the scrap on can be calculated from the resistivity.

20 Claims, 1 Drawing Sheet

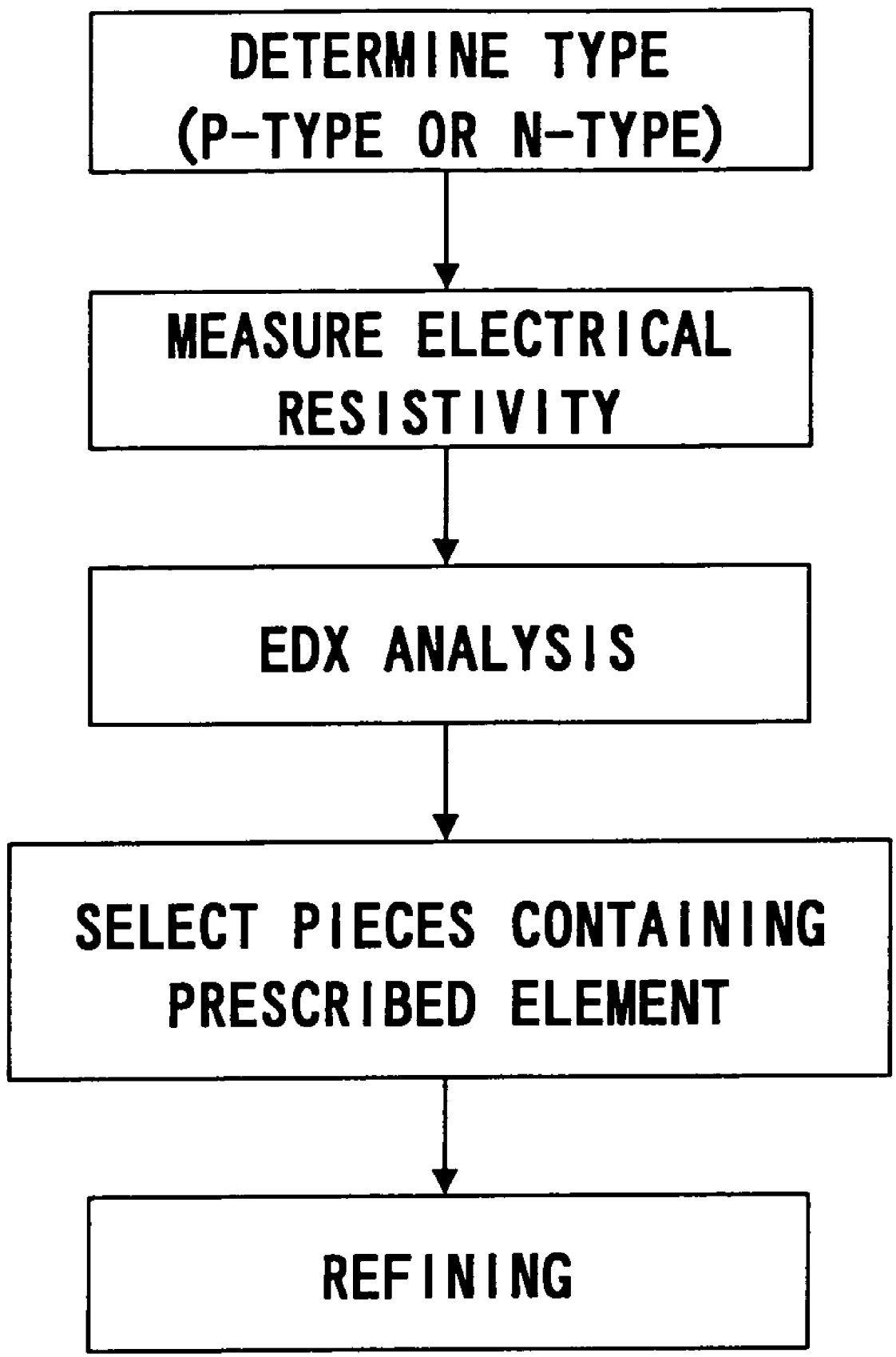

METHOD OF SELECTING AND ANALYZING SCRAP SILICON

BACKGROUND OF THE INVENTION

This invention relates to a method of selecting pieces of scrap silicon containing a prescribed impurity element from a plurality of pieces of scrap silicon containing a variety of impurity elements. It also relates to a method of analyzing scrap silicon to determine the impurity elements contained therein and the contents of the impurity elements.

In order to increase the rate of utilization of silicon, it is desirable to reutilize scrap which is formed during the manufacture of silicon ingots (referred to below as "scrap silicon"). Some scrap silicon contains a large amount of impurities, so it is necessary to increase the purity of scrap silicon before it can be reused.

Semiconductor silicon can be generally divided into n-type semiconductor silicon which uses electrons as mobile charge carriers and p-type semiconductor silicon which uses holes as mobile charge carriers. P-type semiconductor silicon usually contains boron, which has one less valence electron per atom than silicon, as an additive (referred to as a dopant). In contrast, n-type semiconductor silicon usually contains phosphorus (P), arsenic (As), or antimony (Sb), which have one more valence electron per atom than silicon, as an additive.

Accordingly, various types of scrap silicon containing different additives such as boron, arsenic, antimony, and phosphorus in various amounts are formed during the manufacture of silicon products. Since boron forms p-type semiconductor silicon while arsenic, antimony, and phosphorus form n-type semiconductor silicon, semiconductor silicon containing boron as an additive can be easily differentiated from silicon containing arsenic, antimony, or phosphorus as an additive by determining whether a piece of silicon is p-type or n-type using a conventional p-type/n-type checker. If n-type semiconductor silicon can be differentiated from p-type semiconductor silicon, the n-type semiconductor silicon can then be refined in accordance with the type of additive contained therein. From the standpoint of refining, the additives contained in scrap silicon are impurities, so they will be referred to below as impurities or impurity elements.

In the past, in order to refine scrap silicon, n-type scrap silicon was first separated from p-type semiconductor silicon using a p-type/n-type checker, and then the resistivity of individual pieces of scrap silicon was measured. Based on the resistivity, pieces of n-type scrap silicon containing a prescribed impurity element which could be efficiently removed by refining were selected, and the concentration of the impurity element in the pieces after sorting was calculated based on the measured resistivity. The pieces of silicon were then refined under conditions suitable for the calculated concentration. Pieces of silicon containing different types of impurities can to a certain extent be differentiated from each other by measuring resistivity because different types of impurities produce different resistivities. In general, silicon containing arsenic as an impurity has an electrical resistivity of at most 5 milliohm-cm, silicon containing antimony as an impurity has an electrical resistivity from 10 milliohm-cm to 30 milliohm-cm, and silicon containing phosphorus as an impurity has an electrical resistivity of at least 50 milliohm-cm. The relationship between electrical resistivity and the concentration of charge carriers is well known, so if it is assumed that a piece of silicon contains a single impurity, it is easy to calculate the concentration of the impurity from the concentration of carrier electrons.

Recently, however, the above-described impurities have been added in different amounts from in the past so that the ranges of electrical resistivity for different impurity elements may overlap each other. As a result, a given value of electrical resistivity for a piece of scrap silicon may not uniquely identify which impurity element is contained in the piece. Thus, it may be difficult to identify the impurity element in a piece of scrap silicon and to estimate the concentration of the impurity element from a measurement of electrical resistivity alone.

It is conceivable to solve the above-described problem by using an inductively coupled plasma (ICP) emission spectral analyzer to carry out more precise analysis of impurity elements in scrap silicon. However, analysis using an inductively coupled plasma emission spectral analyzer requires a considerable length of time for preparation of specimens prior to analysis. Analysis of impurity elements in silicon can also be carried out by the complete reflection fluorescent x-ray analysis method, but the content of impurity elements in pieces of scrap silicon which do not have a smooth surface cannot be analyzed by this method. Since the content of impurities in scrap silicon is minute, it is not possible to perform analysis by other usual methods of physical analysis.

SUMMARY OF THE INVENTION

In light of the above-described problems of the prior art, the present invention provides a method of easily selecting pieces of scrap silicon containing a prescribed impurity element with certainty and in a short length of time. The present invention also provides a method which makes it possible to analyze pieces of scrap silicon and identity the impurity elements in the scrap silicon in a non-destructive manner and to determine the concentrations of the impurity elements.

The present inventors found that when the concentrations of impurity elements in scrap silicon are in certain ranges, the impurity elements can be identified from a spectrum obtained using an energy dispersive x-ray (EDX) fluorescent analyzer. Below, this device will be referred to for simplicity as an EDX analyzer, and testing using an EDX analyzer will be referred to as EDX analysis. When the concentrations of impurity elements are in certain other ranges, impurity elements in scrap silicon can be identified by combining use of an EDX analyzer with measurement of electrical resistivity. The concentration of an impurity element can be calculated from the measured resistivity.

An EDX analyzer was not developed for analysis of elements having a low concentration, such as impurity elements contained in semiconductor silicon, so determination of the concentration of such impurity elements is not always possible. For this reason, there have been no reports of using an EDX analyzer for sorting scrap silicon in the prior art. As a result of studying the properties of an EDX analyzer, the present inventors discovered that even though an EDX analyzer cannot accurately measure the concentration of elements having a low concentration such as the impurity elements contained in scrap silicon, from the spectral data which is obtained, the presence of impurity elements can be accurately determined when the concentrations of the impurity elements are in certain ranges. Based on the spectral data, pieces of scrap silicon containing a prescribed impurity element can be selected and separated from pieces containing different impurity elements.

According to one form of the present invention, a method of selecting scrap silicon containing a prescribed impurity element from a plurality of pieces of scrap silicon includes applying non-destructive testing to individual pieces of scrap silicon using an energy dispersive x-ray fluorescent analyzer, determining whether the prescribed impurity element is present in a piece based on the obtained spectral data, and selecting pieces containing the prescribed impurity element based on the results of the determination.

Prior to performing non-destructive testing of scrap silicon with an EDX analyzer, it is possible to measure the resistivity of each piece of scrap silicon so as to perform initial selection of pieces of scrap silicon having a greater likelihood of containing a prescribed impurity element. EDX analysis can then be performed to confirm the presence of the prescribed impurity element.

In accordance with another form of the present invention, a method of identifying an impurity element contained in scrap silicon and measuring the content thereof includes applying non-destructive testing to scrap silicon using an EDX analyzer, identifying the impurity elements contained in the scrap silicon from the obtained spectral data, measuring the resistivity of the scrap silicon, and determining the concentration of the impurity elements based on the measured resistivity.

A method according to the present invention employs an EDX analyzer, which performs testing in a non-destructive manner, so analysis of scrap silicon can be carried out much more easily than with a method using an inductive coupling plasma emission spectral analyzer, which requires a considerable length of time for preparing a specimen prior to analysis. When a method according to the present invention combines analysis using an EDX analyzer with the results of measurement of electrical resistivity, the accuracy of analysis can be increased, and the type of impurity element present in a piece of scrap silicon as well as the content thereof can be determined.

BRIEF DESCRIPTION OF THE DRAWING

The sole FIGURE is a flow chart of an embodiment of a method of sorting scrap silicon according to the present invention.

DESCRIPTION OF PREFERRED EMBODIMENTS

An embodiment of a method of selecting scrap silicon containing a prescribed impurity according to the present invention will now be described. In general, each piece of scrap silicon contains only one of boron (B), antimony (Sb), arsenic (As), or phosphorus (P). Therefore, in the following description, it will be assumed that each piece of scrap silicon being analyzed contains a single one of these four elements, and that if the piece of scrap silicon is n-type, it contains a single one of antimony, arsenic, and phosphorus.

When scrap silicon is refined for reuse, speed and ease of refinement as well as the amount of electrical power consumed during refining are important considerations. At present, there is no simple and economical process for refining p-type silicon containing boron. Therefore, pieces of scrap silicon containing boron are usually separated from other pieces and then discarded. Among pieces of n-type scrap silicon, those containing antimony are the easiest to refine by an electron beam refining process in which scrap silicon is irradiated with an electron beam and melted to evaporate impurity elements. Pieces of scrap silicon containing arsenic or phosphorus are also capable of being refined by electron beam refining, but they take a longer time to refine than pieces containing antimony, which means that a larger amount of electrical power is consumed for refinement. Furthermore, if pieces of scrap silicon containing arsenic or phosphorus (particularly, those containing phosphorus) are intermixed with pieces of scrap silicon containing antimony, it takes a long time to complete refining using an electron beam.

Therefore, before pieces of scrap silicon are subjected to refining with an electron beam, typically the pieces are subjected to a sorting process in which pieces containing a prescribed impurity element are selected so that pieces of silicon containing different impurity elements are not intermixed with each other. Which pieces are selected will usually depend upon cost considerations, including the purchase price of scrap silicon and the sale price of refined silicon, which will determine whether pieces of scrap silicon containing a certain impurity element can be refined profitably. Pieces of scrap silicon containing impurity elements which prevent them from being profitably refined can be discarded or used for purposes not requiring refining.

A method according to the present invention employs an EDX analyzer to identify impurities in scrap silicon to determine whether a piece of scrap silicon should be selected for refining. In some cases, a piece of silicon can be selected based entirely on the result of analysis with an EDX analyzer. In other cases, a piece of scrap silicon can be selected based on the result of analysis with an EDX analyzer combined with the result of measurement of electrical resistivity of the piece of scrap silicon.

The sensitivity of an EDX analyzer, i.e., the ability to detect the presence of an impurity element in scrap silicon, varies with the impurity element. In general, an EDX analyzer can detect the presence of 100 ppm or higher of arsenic or 50 ppm or higher of antimony. The peak of phosphorus in EDX analysis is close to that of silicon, so the ability of an EDX analyzer to detect phosphorus is lower than its ability to detect antimony or arsenic, but phosphorus can still be detected in scrap silicon if its concentration as an impurity is at least about 200 ppm.

An electrical resistivity of 5 milliohm-cm or less for a piece of scrap silicon corresponds to an arsenic concentration in the silicon of at least 500 ppm, an antimony concentration in the silicon of at least 800 ppm, or a phosphorus concentration in the silicon greater than 200 ppm. Each of these concentrations is greater than the lower limit for detection of the element using an EDX analyzer, so if a piece of scrap silicon having an electrical resistivity of 5 milliohm-cm or less is tested using an EDX analyzer, it is possible to detect a peak corresponding to arsenic, a peak corresponding to antimony, or a peak corresponding to phosphorus in the spectral graph or data, depending upon which of arsenic, antimony, and phosphorus is present in the piece. In this manner, it is possible to determine whether the piece of scrap silicon contains arsenic, antimony, or phosphorus.

An electrical resistivity of about 10 milliohm-cm for a piece of scrap silicon (which is at the lower end of the typical range of electrical resistivities of pieces of scrap silicon containing antimony) corresponds to an arsenic concentration of about 200 ppm, an antimony concentration of about 400 ppm, or a phosphorus concentration of about 100 ppm. A concentration of 200 ppm of arsenic and a concentration of 400 ppm for antimony are greater than the lower limits for detection of these elements using an EDX analyzer, but a concentration of 100 ppm for phosphorus is below the lower limit for detection of phosphorus. Therefore, if a piece of scrap silicon having an electrical resistivity of about 10 milliohm-cm is subjected to testing using an EDX analyzer, it is possible to detect a peak corresponding to arsenic if the piece contains arsenic or a peak corresponding to antimony if the piece contains antimony. However, if the piece contains phosphorus, it is not possible to detect a peak corresponding to phosphorus due to the low concentration of phosphorus in the piece. In this case, EDX analysis will not produce a peak for any of arsenic, antimony, or phosphorus. However, it can be assumed that the piece of scrap silicon contains phosphorus, since as stated above it is assumed that each piece of n-type silicon being tested contains one of antimony, arsenic, and phosphorus.

An electrical resistivity of about 30 milliohm-cm for a piece of scrap silicon (which is at the upper end of the typical range of electrical resistivities of pieces of scrap silicon containing antimony) corresponds to an arsenic concentration of about 30 ppm, an antimony concentration of about 50 ppm, or a phosphorus concentration of about 10 ppm. An EDX analyzer is still capable of detecting the presence of about 50 ppm of antimony in silicon, but it is not capable of detecting the presence of about 30 ppm of arsenic or about 10 ppm of phosphorus. Therefore, if a piece of scrap silicon with an electrical resistivity of about 30 milliohm-cm is subjected to testing with an EDX analyzer, it is possible to detect a peak corresponding to antimony if antimony is present, but no peak corresponding to any of arsenic, antimony, or phosphorus can be detected when the piece of scrap silicon contains arsenic or phosphorus. Since it is assumed that each piece of n-type scrap silicon being tested contains one of arsenic, antimony, and phosphorus, in this case, it can be assumed that the piece of scrap silicon being tested contains either arsenic or phosphorus, i.e., that it does not contain antimony.

An electrical resistivity of about 50 milliohm-cm for a piece of scrap silicon corresponds to a concentration of 10 ppm or below for any of arsenic, antimony, or phosphorus which is present in the silicon. A concentration of 10 ppm is well below the detectable limit for any of these elements using an EDX analyzer, so it is not possible to ascertain which of these impurity elements is present in a piece of scrap silicon using the method applicable for higher concentrations of these impurity elements. However, at these low concentrations, it may still be profitable to refine the scrap silicon even without knowing beforehand which impurity elements are present, depending upon the cost of scrap silicon and refined silicon.

The following table summarizes the above-described procedure for determining which impurity elements are present in a piece of scrap silicon based on a combination of testing with an EDX analyzer and testing of electrical resistivity ($\rho$). Rx indicates the electrical resistivity of a piece of silicon containing 100 ppm of arsenic, which as stated above is the lowest concentration of arsenic which can be detected in silicon using an EDX analyzer.

| Electrical resistivity ($\rho$) in milliohm-cm of piece of scrap silicon | Element for which peak is detected in piece using EDX analyzer | Type of impurity present in piece |
| --- | --- | --- |
| $\rho \leq 5$ | Sb | Sb |
| | As | As |
| | P | P |
| $5 < \rho \leq Rx$ | Sb | Sb |
| | As | As |
| | no peak detected for As, Sb, or P | P |
| $Rx < \rho \leq 50$ | Sb | Sb |
| | no peak detected for As, Sb, or P | Either As or P |
| $50 < \rho$ | no peak detected for As, Sb, or P | One of As, Sb, or P |

From this table, it can be seen that the presence of antimony in a piece of scrap silicon can be ascertained using an EDX analyzer when the resistivity of the piece is at most 50 milliohm-cm, while the presence of arsenic or phosphorus can be ascertained when the resistivity of the piece is at most Rx. At a resistivity of greater than Rx, it is possible to ascertain whether arsenic or phosphorus may be present in a piece, but it is not possible to determine by this method which of the two is present for certain, and at a resistivity of greater than 50 milliohm-cm, it is not possible to ascertain by this method which of antimony, arsenic, or phosphorus is present.

In situations in which it is desired to identify only pieces of scrap silicon containing antimony and it is not necessary to determine the concentration of the antimony, it is sufficient to employ EDX analysis of pieces of silicon without measuring their resistivity. When it is desired to also determine the concentration of antimony in pieces of scrap silicon or to identify pieces of scrap silicon containing impurity elements other than antimony, EDX analysis can be combined with measurement of resistivity. It does not matter whether measurement of the resistivity is performed before after EDX analysis. Once the results of EDX analysis and measurement of resistivity of a piece of scrap silicon are obtained, it can be determined from the above table whether the piece contains a prescribed impurity element. If the prescribed impurity element is present, then the piece can be selected, i.e., placed apart from pieces not containing the prescribed impurity element so that it can be refined or otherwise treated separately from those pieces. Refinement of pieces of silicon which have been selected will typically be carried out by the electron beam refining method, but any other convenient refining method can also be used.

The attached figure is a flow chart of one example of a method of selecting pieces of scrap silicon for refining according to the present invention. In a first step, pieces of scrap silicon are individually tested with a conventional p-type/n-type checker (such as a model PN-12 alpha sold by Napson Corporation) to determine whether each piece is n-type or p-type silicon. The n-type scrap silicon is set aside for further testing, while the p-type silicon may be discarded.

Next, the electrical resistivity of each piece of n-type silicon is measured using a conventional resistivity tester, after which each piece is tested using a conventional EDX analyzer (such as a model EDX-700HS manufactured by Shimadzu Manufacturing Company) to determine whether a peak corresponding to arsenic, antimony, or phosphorus is present in the resulting spectral data for the silicon. In some cases, no peak corresponding to any of the three elements will be present when the concentration of the impurity elements is below the detectable limit of the EDX analyzer.

Then, referring to the above table, it is determined whether each piece contains a prescribed impurity element. If a piece contains the prescribed impurity element, it is selected and set aside for refining. The pieces of scrap silicon which are not selected can be discarded or otherwise disposed of.

Based on the measured resistivity, it is possible to calculate the concentration of the prescribed impurity element in each piece of scrap silicon which was selected. Therefore, prior to refining the selected pieces of scrap silicon, if desired, they can be sorted, i.e., divided into groups according to the concentration of the prescribed impurity element contained therein, and the different groups can be refined separately from each other to increase the efficiency of refining operations. Alternatively, groups of pieces of silicon having a concentration of the prescribed impurity element which renders the pieces of scrap silicon uneconomical to refine can be discarded or otherwise disposed of without being refined.

Each of the pieces of scrap silicon which is subjected to measurement of resistivity may be subjected to EDX analysis. However, although an impurity element may be present in silicon over a wide range of concentrations, it is more likely to be present in silicon in a prescribed concentration range corresponding to a prescribed range of resistivities. In order to reduce the number of pieces of scrap silicon which are subjected to EDX analysis, measurement of electrical resistivity can be performed prior to EDX analysis, and only pieces of scrap silicon having a resistivity in a prescribed range can be subjected to EDX analysis, with pieces of scrap silicon having a resistivity outside of this range being discarded or otherwise disposed of. For example, the resistivity of scrap silicon containing antimony is most commonly in the range of 10 to 30 milliohm-cm. When the method shown in the figure is being used to select pieces of scrap silicon containing only antimony, only pieces of scrap silicon having a resistivity of 10 to 30 milliohm-cm in the step of measuring resistivity can be passed on to the step of EDX analysis, and other pieces can be discarded. EDX analysis can then be performed on each piece of scrap silicon having a resistivity of 10 to 30 milliohm-cm to ascertain which of those pieces contains antimony, and those containing antimony can then be selected for refinement.

Although the attached figure shows measurement of electrical resistivity being carried out before EDX analysis, as stated above, measurement of electrical resistivity may be carried out after EDX analysis.

A method of selecting pieces of scrap silicon for refining according to the present invention will be further described by the following examples.

EXAMPLE 1

Pieces of scrap silicon formed during the manufacture of silicon ingots are used as a starting material. Initially pieces of p-type and n-type silicon are intermixed in the same container. Each piece of scrap silicon is tested with a p-type/n-type checker to determine its type. Pieces of p-type silicon are discarded, while pieces of n-type silicon continue on to the next step in the method.

Each piece of n-type silicon is then tested using an EDX analyzer. Each piece for which a peak corresponding to antimony is detected is selected for refinement, while all other pieces are discarded.

EXAMPLE 2

In the same manner as in Example 1, pieces of n-type silicon are separated from pieces of p-type silicon, and then pieces of n-type silicon containing antimony are selected by EDX analysis. The electrical resistivity of each selected piece containing antimony is then measured, and the selected pieces are divided into a plurality of groups according to resistivity, with each group containing Sb in a different concentration range. The different groups can be refined separately from each other to increase refining efficiency.

EXAMPLE 3

Pieces of p-type and n-type silicon are separated from each other in the same manner as in Example 1. The pieces of p-type silicon are discarded, and the electrical resistivity of each piece of n-type silicon is measured. Pieces having a resistivity in the range of 10 to 30 milliohm-cm are sent to the next step in the method, while the other pieces are discarded.

The pieces having a resistivity in the range of 10 to 30 milliohm-cm are tested with an EDX analyzer. Pieces in which Sb can be detected are selected for refining, while pieces in which Sb is not detected are discarded.

EXAMPLE 4

In the same manner as in Example 2, pieces of scrap silicon are divided into p-type and n-type. The pieces of p-type are discarded. The electrical resistivity of each piece of n-type silicon is measured, and then each pieces is tested with an EDX analyzer. Referring to the above table, each piece is then classified based on the resistivity and the results of EDX analysis in one of the following groups: (a) pieces containing antimony, (b) pieces containing arsenic, (c) pieces containing phosphorus, (d) pieces having a resistivity of at most 50 milliohm-cm and containing one of arsenic and phosphorus but for which it cannot be ascertained which of the two elements is present, and (e) pieces having a resistivity of greater than 50 milliohm-cm. The pieces of the different groups (a)-(e) are disposed of as follows. The pieces of group (a) are always refined. The pieces of group (b) are refined only when they can be refined profitably, but refined separately from the pieces of group (a) because of the difference in time required for refinement. The pieces of groups (c), (d) or (e) are usually discarded. However, they may be refined when their impurity concentrations are low and they can be refined profitably.

As described above, a method according to the present invention can reliably select pieces of scrap silicon containing a prescribed impurity element, so it enables scrap silicon to be more efficiently and economically refined to significantly increase the rate of utilization of scrap silicon.

What is claimed is:

1. A method of selecting scrap silicon containing a prescribed impurity element from a plurality of pieces of scrap silicon, comprising applying non-destructive testing to individual pieces of scrap silicon using an energy dispersive x-ray fluorescent analyzer, determining whether the prescribed impurity element is present in a piece based on the obtained spectral data, and selecting pieces containing the prescribed impurity element based on the results of the determination.

2. A method of selecting scrap silicon as claimed in claim 1 including measuring the electrical resistivity of a piece of the scrap silicon and then testing the piece with the energy dispersive x-ray fluorescent analyzer only if the resistivity of the piece is within a prescribed range.

3. A method of selecting scrap silicon as claimed in claim 2 wherein the prescribed range is consistent with the presence of the prescribed impurity element in the tested piece.

4. A method of selecting scrap silicon as claimed in claim 1 including tasting only pieces of n-type scrap silicon with the energy dispersive x-ray fluorescent analyzer.

5. A method of selecting scrap silicon as claimed in claim 4 wherein the prescribed impurity element is antimony or arsenic.

6. A method of selecting scrap silicon as claimed in, claim 1, wherein each piece of scrap silicon is n-type silicon, and the prescribed impurity element is phosphorus.

7. A method of selecting scrap silicon as claimed in claim 1 including refining the selected pieces separately from pieces containing an impurity other than the prescribed impurity element to remove the prescribed impurity element.

8. A method of selecting scrap silicon as claimed in claim 1 wherein the scrap silicon is scrap formed during the manufacture of a silicon ingot.

9. A method of selecting scrap silicon as claimed in claim 1 including measuring the electrical resistivity of each piece of scrap silicon and determining whether the prescribed impurity element is present in a piece based on the spectral data for the piece and the electrical resistivity of the piece.

10. A method of selecting scrap silicon as claimed in claim 9 including determining that a piece of scrap silicon contains P when the spectral data for the piece does not indicate the presence of P, As, or Sb and the electrical resistivity $\rho$ of the piece is in the range of 5 milliohm-cm$<\rho\leq$Rx, wherein Rx indicates the electrical resistivity of a piece of silicon containing 100 ppm of arsenic.

11. A method of selecting scrap silicon as claimed in claim 9 including determining that a piece of scrap silicon contains one of As and P when the spectral data for the piece does not indicate the presence of P, As, or Sb and the electrical resistivity $\rho$ of the piece is in the range of Rx$<\rho\leq$50 milliohm-cm, wherein Rx indicates the electrical resistivity of a piece of silicon containing 100 ppm of arsenic.

12. A method of selecting scrap silicon as claimed in claim 1 including measuring the electrical resistivity of the selected pieces of scrap silicon and sorting the selected pieces into groups according to the concentration of the prescribed impurity element in the selected pieces based on the measured electrical resistivity.

13. A method of selecting scrap silicon as claimed in claim 12 including refining the different groups separately from each other to remove the prescribed impurity element.

14. A method of identifying an impurity element contained in scrap silicon comprising:
applying non-destructive testing with an energy dispersive x-ray fluorescent analyzer to a piece of n-type scrap silicon formed during manufacture of a silicon ingot to obtain spectral data for the piece,
measuring the electrical resistivity of the piece of scrap silicon, and
determining whether the piece of scrap silicon contains Sb, As, or P based on the spectral data and the measured electrical resistivity.

15. A method of selecting scrap silicon for refining comprising:
testing a plurality of pieces of n-type scrap silicon formed during the manufacture of a silicon ingot with an energy dispersive x-ray fluorescent analyzer to obtain spectral data;
determining whether each piece contains a prescribed impurity element selected from Sb, As, and P based on the spectral data; and
separating the pieces containing the prescribed impurity element from the other pieces.

16. A method of selecting scrap silicon as claimed in claim 15 further comprising refining the pieces containing the prescribed impurity element separately from pieces containing a different impurity element.

17. A method of selecting scrap silicon as claimed in claim 15 including determining whether each tested piece of scrap silicon contains Sb, As, or P and sorting the tested pieces according to the impurity element contained therein.

18. A method of selecting scrap silicon as claimed in claim 15 including measuring the electrical resistivity of the pieces containing the prescribed impurity element and sorting the pieces containing the prescribed impurity element into groups according to the concentration of the prescribed impurity element in the pieces containing the prescribed impurity element based on the measured electrical resistivity.

19. A method of selecting scrap silicon as claimed in claim 18 including refining the different groups separately from each other to remove the prescribed impurity element.

20. A method of selecting scrap silicon as claimed in claim 15 including determining which of Sb, As, or P is contained in a piece of scrap silicon based on the electrical resistivity of the piece when the spectral data for the piece does not indicate the presence of Sb, As, or P in the piece.

* * * * *